US007860581B2

(12) United States Patent
Eckerdal et al.

(10) Patent No.: US 7,860,581 B2
(45) Date of Patent: Dec. 28, 2010

(54) IMPLANTABLE LEAD WITH A STIMULATING ELECTRODE AND A MAPPING ELECTRODE THAT IS ELECTRICALLY DISCONNECTABLE

(75) Inventors: Johan Eckerdal, Knivsta (SE); Kenneth Dahlberg, Stockholm (SE)

(73) Assignee: St. Jude Medical AB, Jarfalla (SE)

( * ) Notice: Subject to any disclaimer, the term of this patent is extended or adjusted under 35 U.S.C. 154(b) by 443 days.

(21) Appl. No.: 12/090,982

(22) PCT Filed: Oct. 31, 2005

(86) PCT No.: PCT/SE2005/001630

§ 371 (c)(1),
(2), (4) Date: Apr. 21, 2008

(87) PCT Pub. No.: WO2007/053065

PCT Pub. Date: May 10, 2007

(65) Prior Publication Data

US 2008/0288040 A1    Nov. 20, 2008

(51) Int. Cl.
*A61N 1/05* (2006.01)
(52) U.S. Cl. ...................... 607/127; 600/375
(58) Field of Classification Search ............. 607/127
See application file for complete search history.

(56) References Cited

U.S. PATENT DOCUMENTS

| 4,402,223 | A  | * | 9/1983  | Naumann et al. ............. 73/625 |
| 5,824,030 | A  |   | 10/1998 | Yang et al. |
| 6,418,348 | B1 | * | 7/2002  | Witte ......................... 607/122 |
| 6,421,567 | B1 |   | 7/2002  | Witte |
| 6,459,937 | B1 |   | 10/2002 | Morgan et al. |
| 6,529,779 | B1 |   | 3/2003  | Sutton |
| 2005/0038491 | A1 |   | 2/2005 | Haack |
| 2005/0137671 | A1 |   | 6/2005 | Liu et al. |

FOREIGN PATENT DOCUMENTS

WO    WO 99/43381    9/1999

* cited by examiner

*Primary Examiner*—Kennedy J Schaetzle
(74) *Attorney, Agent, or Firm*—Schiff Hardin LLP

(57) ABSTRACT

An implantable lead for delivering electrical stimuli to a human heart has a stimulating electrode for transmitting electrical stimuli to the myocardium after implantation, and a mapping electrode for use during implantation. The mapping electrode is configured to deliver electrical stimuli to the heart and to sense intrinsic cardiac activity, for the purpose of finding a suitable fixation position in the myocardium. During the implantation procedure, the mapping electrode is electrically connected to the conductor. The lead is configured to electrically disconnect the mapping electrode from the conductor after a suitable fixation position has been determined.

19 Claims, 5 Drawing Sheets

IMPLANTABLE LEAD WITH A STIMULATING ELECTRODE AND A MAPPING ELECTRODE THAT IS ELECTRICALLY DISCONNECTABLE

BACKGROUND OF THE INVENTION

1. Field of the Invention

The present invention generally relates to the field of implantable medical devices. More specifically, the present invention relates to an implantable lead for delivering electrical stimuli to a human heart, the lead having a proximal end for connection to an implantable medical device, and a distal end for fixation in the myocardium of a human heart.

2. Description of the Prior Art

Within the field of implantable heart stimulators, such as pacemakers, implantable leads are used for conveying electrical stimuli from the heart stimulator to the myocardium of a human heart. Before fixation of an implantable lead to a location in myocardial tissue of a human heart, the physician is interested in knowing whether the selected location is suitable for delivering electrical stimuli and possibly also for sensing electric intrinsic activity, i.e. electrical activity of the heart which is not induced by stimulation pulses from the medical implant. In other words, the physician must know whether delivered electrical stimuli at the selected position will provide a desirable response in the myocardial tissue, and will measurements of intrinsic activity provide a sufficiently strong signal at the selected position? This is conventionally performed by fixating the distal end of the implantable lead to the tissue, sensing intrinsic cardiac activity and/or delivering stimulation pulses and monitoring the response of the heart, i.e. the evoked response. If the results are not satisfactory, the lead could be disengaged from the myocardial tissue and repositioned to another location within the heart. However, this procedure may be time-consuming and cause unnecessary trauma to the endocardial and myocardial tissue.

Recently, a method of finding a suitable location has been developed in which the distal end of an implantable lead is arranged with an electrode surface intended for delivering electrical stimuli to the heart and intrinsic cardiac activity is sensed without the need of fixating the electrode in the myocardial tissue. In this prior art implantable lead, the distal end of the lead is provided with an electrode end surface for contacting endocardial or myocardial tissue. Thereby, a stimulating electrode, such as an extendible and retractable helix, could remain in the retracted state, with no or very little contact with myocardial tissue, while the electrode end surface was used for contacting myocardial tissue for the purpose of locating a suitable fixation location in the heart. In practice, the stimulating electrode is provided with a movable portion for fixation of the lead, for contacting and for delivering stimulating pulses to the myocardium after implantation, and a stationary portion for contacting and delivering stimulation pulses during implantation. Commonly, the movable portion is an extendible and retractable helix arranged within the distal end of the lead and extendible therefrom, and the stationary portion is arranged annularly at the distal end of the lead encircling the helix.

As a consequence, no retraction of the helix and repositioning of the distal end of the lead was required for finding a suitable fixation position. However, the presence of an electrode surface intended for use when finding a suitable fixation location has been observed to have an impact on the energy consumption of a medical implant.

SUMMARY OF THE INVENTION

An object of the present invention is to provide an improved implantable lead for fixation to the myocardium of the heart.

According to an aspect of the present invention, an implantable lead for delivering electrical stimuli to a human heart has a proximal end for connection to an implantable medical device, a distal end for fixation in the myocardium of a human heart, an insulating flexible tube extending from the proximal to the distal end, and a conductor arranged in the flexible tube and extending from the proximal to the distal end for conducting the electrical stimuli from the medical device to the heart and for conducting sensed intrinsic cardiac signals from the heart to the medical implant. The distal end has a fixation arrangement for the fixation of the distal end in the myocardium, a stimulating electrode for transmitting said electrical stimuli to the myocardium after implantation, and a mapping electrode for transmitting the electrical stimuli to the myocardium and/or sensing intrinsic cardiac activity during implantation for finding a suitable fixation position in the myocardium. The mapping electrode is electrically connected to said conductor during implantation, and the lead is arranged for electrically disconnecting the mapping electrode from the conductor.

Thus, the invention is based on the advantageous insight of providing a separate electrode intended to be used solely for delivering electrical stimuli and sensing intrinsic cardiac activity during the implantation procedure, for the purpose of finding a suitable location for fixation of the implantable lead, and for electrically disconnecting said electrode from the medical implant, i.e. heart stimulator, and the stimulating electrode when the lead has been fixed to the myocardium of the heart. Such an electrode will in the following be referred to as a mapping electrode, since it is used during mapping, i.e. measuring and evaluating at different locations of the heart. The mapping procedure may include measurements of stimulation thresholds and/or intrinsic cardiac activity characteristics.

It should be noted that the phrase "electrically disconnecting" refers to the interruption of an electrical conducting path and is no indication of how the actual disconnecting is performed. For instance, an unplugging of an electrical cord would in this context be regarded as "electrically disconnecting", even when performed by mechanical means or manually.

Furthermore, the term "conductor" refers to a single conductor arranged within and extending through the lead for conducting electrical stimulation pulses, e.g. pacing pulses, from the medical implant to the distally arranged stimulating electrode and mapping electrodes. However, the implantable lead can carry further conductors, such as connected to sensing electrodes, which will not be discussed further herein.

An advantage of providing a separate, electrically disconnectable mapping electrode resides in the enabled reduction of the contact surface area between the stimulating surfaces of the distal lead end and the myocardial tissue following implantation of the medical device. Thus, following implantation and fixation of the distal end of the implantable lead at a suitable location in the heart, the mapping electrode is electrically disconnected from the heart stimulator, such that only the electrode intended for stimulation at said location is connected for delivering electrical stimuli to the myocardial tissue. Thereby, the impedance between the stimulating electrode surfaces and the myocardial tissue is increased, which results in the energy content required for evoking a response in the myocardial tissue being reduced. This, in turn, results in a reduction of the overall energy consumption of the heart stimulator.

During implantation of an implantable ventricular lead intended for implantation in a ventricle of a human heart, the implantable lead is fed to the heart, generally through the superior vena cava, through the atrium, and introduced into the ventricle of the heart. The lead is advanced until the distal end thereof is brought into contact with the myocardial tissue. Upon reaching an intended location for fixation, a mapping procedure is initiated and stimulation pulses are delivered to the myocardium using the mapping electrode of the lead. At this point, the mapping electrode is in electrical connection with the medical implant via the conductor. The resulting myocardial response, i.e. the evoked response, is detected and evaluated. Alternatively, the mapping procedure could also include measuring or sensing intrinsic electrical cardiac activity, and evaluating the quality and signal strength of the measured intrinsic activity signal. As a further option, the mapping procedure could be limited to the sensing and evaluating intrinsic cardiac activity signals. Then, no stimulation pulses are delivered during the mapping procedure.

If the evaluation determines that delivered stimuli at the present location do not provide satisfactory myocardial responses or that the measurements of intrinsic cardiac activity does not provide a satisfactory signal, the distal end of the lead is repositioned at another location and the mapping procedure is repeated. This is performed until a suitable location is found where satisfactory results are provided. Upon finding a suitable location, the distal end of the lead is fixed to the myocardium and the mapping electrode is electrically disconnected from the conductor and the medical implant.

It should be noted that the present invention is not restricted to ventricular leads. An atrial lead intended for positioning and fixation in an atrium of the heart is within the scope of the present invention. Thus, the description of the general operation of the lead, as described above in relation to a ventricular lead, also applies to an atrial lead, apart from the passage of introducing the atrium into the ventricle. However, for ease of description and understanding, the following description and the embodiments will be based on a ventricular lead.

According to embodiments of the invention, the implantable lead is arranged for disconnecting said mapping electrode during the actual fixation of the lead to the myocardium. Then, the handling of the fixation arrangement for achieving the distal end fixation preferably also provides the electrical disconnection of the mapping electrode. In other words, no separate manipulation of the lead is required for accomplishing the electrical disconnection of the mapping electrode from the conductor conveying stimulation pulses from the heart stimulator.

Moreover, according to exemplifying embodiments, the fixation of the distal end of the lead is provided by advancing the distal end of the stimulating electrode, sometimes also referred to as a tip electrode, into the myocardial tissue. In practice, the tip electrode is arranged at distal portion of the lead, referred to herein as a header. During implantation, the tip electrode is arranged in a retracted state and situated essentially within the header. When a suitable fixation location has been determined, the tip electrode is advanced beyond the distal end of the header, and into the myocardial tissue where attachment to the myocardium is provided. During the advancing movement of the stimulation or tip electrode, contact between the conductor, to which the mapping electrode is connected, is interrupted by the advancing movement per se.

The stimulating electrode, on the other hand, is either in constant electrical connection with the conductor, or becomes electrically connected to the conductor during the advancing movement of the stimulating electrode in relation to the header. However, according to preferred embodiments of the invention, the stimulating electrode is in constant electrical connection with the conductor.

The electrical disconnection of the mapping electrode can be accomplished in a manner of different ways, as readily understood by those skilled in the art, of which a few exemplifying will be described. However, it should be noted that the scope of the present invention is not restricted to the described examples. On the contrary, further alternatives that would be envisaged by the person skilled in the art are contemplated within the scope of the present invention.

According to first exemplifying embodiments of the invention, the electrical connection to the mapping electrode is interrupted by providing insulated elements in the conduction path. For instance, a movable element, such as the element used for advancing the stimulating electrode, can be provided with conducting and nonconducting or dielectric contact surfaces vis-à-vis conducting contact surfaces of a stationary element, such as the header or a portion thereof, or vice versa. Then, upon movement of the movable element, for instance by translation or rotation, engagement between conducting contacting surfaces of both elements is replaced for engagement between an electrically insulated surface of at least one of the elements and a conducting surface of the other element. Thereby, the conduction path between the movable and the stationary element is interrupted by the relative movement between the two elements.

According to one example, a shaft electrically connected with the conductor is arranged within the hollow interior of a header and provided with a sliding contact that is in engagement with the inner surface of the header. The engagement provides an electrical connection between the shaft and the header, which in turn is electrically connected to the mapping electrode. By advancing the shaft in relation to the header during or following fixation of the lead, the engaging portions of the sliding contact is brought into engagement with an inner surface of the header provided with an electrical insulation. Thereby, the conduction path between the shaft and the header is interrupted, which electrically disconnects the mapping electrode from the conductor.

According to further exemplifying embodiments, two engaging elements located in the conduction path between the conductor of the lead and the mapping electrode could be disengaged by the relative movement between the elements. In one embodiment, a shaft connected to the conductor is provided with a larger diameter at one position along the shaft, and a smaller diameter at another position along the shaft. A flexible, annular contact element in electrical connection with the mapping electrode is provided for engagement with the shaft. The contact element is arranged around the shaft and has an inner diameter which is slightly smaller than the larger diameter of the shaft, but larger than the smaller diameter of the shaft. Thus, when the contact element is located around the larger diameter of the shaft, the shaft and the contact element is in engagement with each other. By advancing the shaft in relation to the contact element such that the contact element becomes located around the smaller diameter of the shaft, the shaft and the contact element becomes disengaged. Examples of contact elements include toroid coil springs, i.e. having the form of annularly arranged helical coils acting as toroid contact springs.

Moreover, according to further examples of the invention, the electrical connection and disconnection between the conductor for conveying electrical stimuli from the medical implant and the mapping electrode could be provided via the stimulating electrode, which in these examples is connected to the conductor during implantation of the lead. Preferably, the stimulating electrode is in these examples permanently electrically connected with the conductor.

According to one embodiment, the stimulating electrode is in engagement with the mapping electrode during implantation of the lead. The engagement is provided via conducting contact surfaces of the respective electrodes such that electrical connection is established between the stimulation and the mapping electrode. Upon advancing the stimulating electrode, portions of the contact surface of the stimulating electrode provided with an isolating surface layer is brought into engagement with the contact surfaces of the mapping electrode. Thereby, the conduction path between the stimulating electrode and the mapping electrode is interrupted. Accordingly, the mapping electrode becomes electrically disconnected from the conductor and, in turn, the heart stimulator.

As understood be the person skilled in the art, the interruption of the conduction path between the mapping electrode and the stimulating electrode could also be provided through geometrical design, i.e. such that the contact surfaces of the respective electrodes becomes disengaged.

Furthermore, according to preferred embodiments of the invention, the stimulating electrode is in the form of an extendible and retractable helix. Thus, by rotation of the helix in relation to the header, the distal end of the helix is extended beyond the header and screwed into the myocardial tissue at the fixation location.

The electrical insulations and dielectric portions referred to above could be provided by forming the relevant portions or elements from a dielectric material, i.e. a non-conducting or electrically insulating material. Alternatively, insulating layers arranged onto conducting surface portions or elements could be provided, for instance by providing the relevant portions with a dielectric or insulating coating. Such a coating could for instance be formed from a dielectric polymer or elastomer, such as ethylene tetrafluoro ethylene (ETFE), polytetrafluoro ethylene (PTFE), parylene, non-polymers, such as diamond like carbon (DLC), or any other dielectric material suitable to be arranged as an insulating coating in the present environment. Furthermore, an insulating surface portion can also be provided by processing a conducting surface material such that insulating surface layer is achieved. Examples of such processing can include oxidation or nitration of a material, such that an insulating oxide or nitride surface layer is obtained, for example aluminum oxide or titanium oxide.

It should be noted that, throughout the specification, reference is made to "an/the implantable lead", "a/the conductor" and "a/the stimulating electrode", respectively. However, the present invention is by no means restricted to medical implants having only one lead, implantable leads having only one conductor, or medical implants having only one stimulating electrode. On the contrary, the invention is suitable for and/or can be combined with any multiple, dual or single chamber heart stimulators, including biventricular stimulators, as long as there is a need for mapping fixation locations of an implantable lead. Also, the implantable lead according to the invention can be provided with further conductors and electrodes, such as electrodes and associated conductors for sensing evoked response, sensors of other physiological parameters and accompanying conductors, etc., without departing from the scope of the present invention.

Furthermore, in the embodiments disclosed herein, a single conductor is used for distributing stimulation pulses to the mapping electrode and the stimulating electrode. Of course, this is also the alternative in the prior art leads having an electrode surface for mapping suitable fixation locations is provided, since said electrode surface is electrically connected to the stimulating electrode used for stimulating the myocardial tissue following implantation. However, even though preferred, the idea of having a disconnectable mapping electrode could be realized in an implantable lead having separate conductors, extending through the lead, for connection to the mapping electrode and to the stimulating electrode, respectively. Then, the disconnection of the mapping electrode could be achieved by interrupting the conduction path at the distal end of the lead, similar to the embodiments described herein, or by simply not delivering any electrical stimuli via the conductor connected to the mapping electrode once the lead has been fixed to a suitable location.

Further features of, and advantages with, the present invention will become apparent when studying the following description and drawings. Those skilled in the art realize that different features of the present invention can be combined to create embodiments other than those described in the following, without departing from the scope of the present invention.

BRIEF DESCRIPTION OF THE DRAWINGS

FIG. 2b is an enlarged, partial view showing a portion of the distal end according to FIG. 2a.

FIG. 3b is an enlarged, partial view showing a portion of the distal end according to FIG. 3a.

DESCRIPTION OF THE PREFERRED EMBODIMENTS

Figure 1:
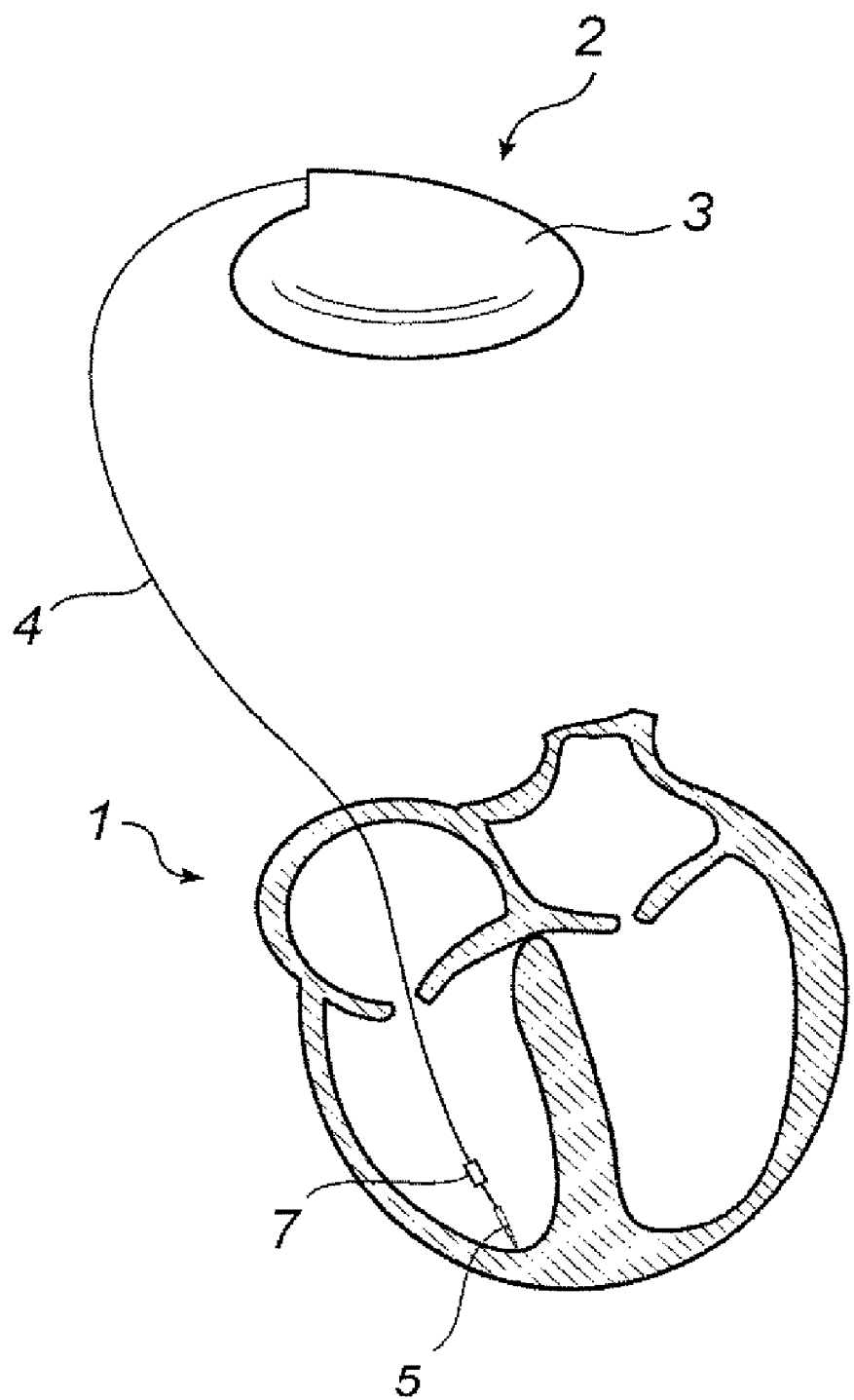
FIG. 1 is a simplified schematic illustration of a medical implant in electrical communication via an implantable lead with a human heart.

The following is a description of exemplifying embodiments in accordance with the present invention. This description is intended for describing the general principles of the invention and is not to be taken in a limiting sense. Like reference numerals indicate structures or elements having same or similar functions or constructional features.

Referring first to FIG. 1, there is shown an implantable heart stimulator 2 in electrical communication with a human heart 1 via a cardiac lead 4 arranged for stimulation and sensing. Moreover, the heart stimulator 2 comprises electronic circuitry and a battery contained within a hermetically sealed pacemaker housing 3. The housing 3 comprises a metallic casing of titanium, enclosing the electronic circuitry and battery, and a molded plastic header portion, comprising connector blocks and apertures for receiving the connectors at the proximal ends of the cardiac leads.

The electronic circuitry comprises at least one pulse generator for generating stimulation pulses, sensing circuitry for receiving cardiac signals sensed by the cardiac lead 4, and a controller. The controller controls both the sensing of cardiac signals and the delivery of stimulation pulses, for instance as to the duration, energy content and timing of the stimulation pulses.

The stimulation pulses generated by the pulse generator are transmitted via the cardiac lead 4 and delivered to the cardiac tissue by the use of tip electrodes positioned at the distal end 5 of the cardiac lead. Generally, the tip electrode acts as the cathode when the cardiac pulse is delivered. Furthermore, in unipolar cardiac systems, the casing 3 acts as the anode, while in bipolar cardiac systems, the anode is provided by an annular or ring electrode 7 arranged on the cardiac lead at a small distance from the tip electrode.

It should be noted that even though a ring electrode 7 is illustrated in the greatly simplified drawing of It should be noted that even though a ring electrode 7 is illustrated in the greatly simplified drawing of FIG. 1, the present invention is equally applicable to unipolar, bipolar, and multipolar systems. Thus, implantable leads with or without ring electrodes are equally contemplated without departing from the scope of the invention. Furthermore, even though only one lead 4 for attachment and stimulation in the right ventricle is illustrated in the drawing, the medical implant 2 may be connected to further leads, for instance for stimulation of the right atrium, the left atrium, and/or the left ventricle.

Figure 2A:
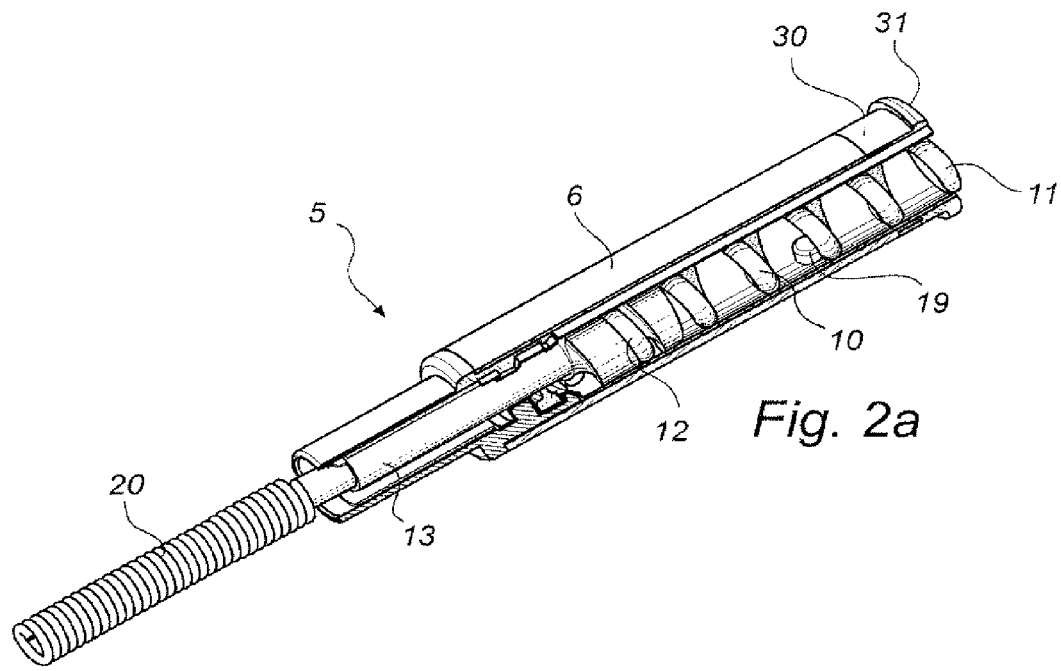
FIG. 2a is a perspective view of a distal end of an implantable lead according to a first embodiment.
Figure 2B:
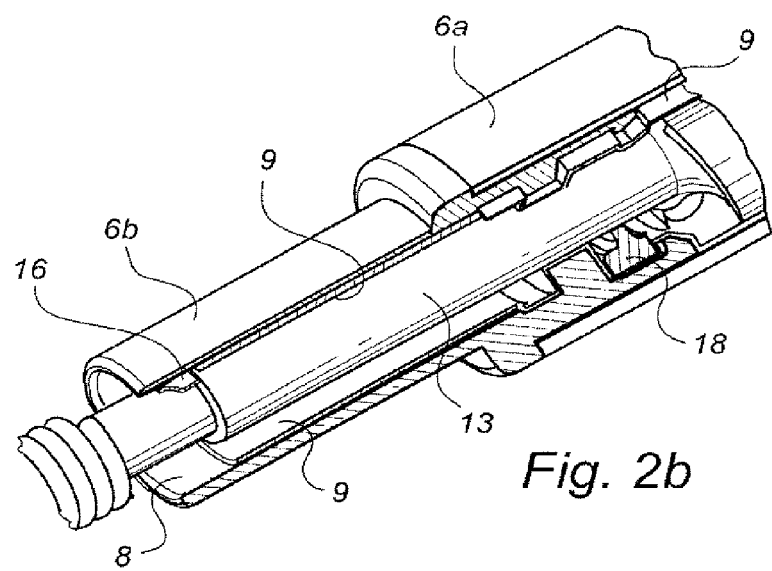

Turning now to FIGS. 2a and 2b, there is shown the distal end 5 of a lead according to a first exemplifying embodiment. The distal end 5 has a header 6 having a general configuration of a cylindrical sleeve. The header 6 is provided a cylindrical header sleeve (not shown) which is formed from an insulating material. Thus, the header sleeve covers the entire length of the header 6 and seals it from surrounding tissue and bodily fluids. The header 6 comprises in this example a distal end 6a of a larger diameter and a proximal end 6b of a smaller diameter.

The distal end 6a incorporates a helical electrode or helix 10 intended for delivering stimulation pulses to the cardiac tissue and/or for sensing electrical cardiac activity in the form of intrinsic activity and/or evoked responses. The helix 10 has a distal end 11 intended to be advanced beyond the distal end 6a of the header 6 and screwed into cardiac tissue for fixation. The advancing motion is accomplished by rotating the helix 10 in relation to the header 6, whereby the engagement between the helix 10 and a post 19 arranged on the inner surface of the hollow header 6 forces the helix 10 to be advanced in relation to the header 6.

A sealing element 18 is further arranged within the header for sealing the proximal portions of the lead from the distal portions thereof, such that bodily fluids or the like are prevented from reaching said proximal portions.

The proximal end 12 of the helix 10 is attached to a shaft 13, which is essentially arranged within the proximal portion 6b of the header 6. The shaft 13 is in turn attached to a conductor 20, in the form of a helically wound coil, for establishing the electrical connection between the medical implant 2 and the helix 10. Thus, electrical connection is provided between the conductor 20, the shaft 13 and the helix 10. An insulating outer tubing (not shown) is provided around the conductor and attached to the header 6. Thus, the conductor 20 and the connecting shaft 13 and helix 10 are rotatable within the tubing (not shown) and header 6.

At the very distal end of the header 6, a mapping electrode 30 is provided. The mapping electrode 30 has an annular configuration and is arranged as a ring or collar at the distal tip of the lead. The mapping electrode 30 has a distally arranged contact surface in the form of a collar portion 31 which is intended for contacting and electrically connecting the lead with cardiac tissue. The insulating outer tubing covering the header 6 extends up to the mapping electrode such that the displayed outer surface of the mapping electrode is limited to the collar portion 31. Furthermore, the mapping electrode is electrically connected to the header 6, which is an electrically conducting element.

The inner surface of the header 6 is further provided with an electrically insulating surface layer 9 for insulating the header from the helix 10 and the shaft 13. The insulating layer 9 extends from the distal end of the header 6, i.e. including the distal portion provided with the mapping electrode 30, to a location near the proximal end 6b of the header. At the proximal end 6b, a surface portion 8 of the header inner surface has been left without any insulating surface layer 9, such that electrical connection may be enabled between the header 6 and the shaft 13.

Furthermore, the shaft 13 is at an end surface 14 thereof provided with a sliding contact 16. The sliding contact 16 constitutes an electrically conducting contact spring which is brought into biased engagement with the inner surface of the header proximal end 6b. Thus, as shown in FIGS. 2a and 2b, the sliding contact 16 provides an electrical connection between the header 6 and the shaft 13, which in turn results in an electrical connection between the conductor 20 and the mapping electrode 30.

During the procedure of fixating the lead distal end 5, the conductor 20, the shaft 13 and the helix 10 are jointly rotated and advanced within the header 6 through the engagement with the post 19. As a result, the sliding contact 16 is transported by the rotating and advancing movement in the distal direction within the lead, such that the engagement between the sliding contact 16 and the conducting surface portion 8 of the header 6, is replaced for an engagement between the sliding contact 16 and a non-conducting or insulating surface layer 9 of the header 6. Thus, the conduction path and the electrical connection established between the conductor 20 and the mapping electrode 30, via the shaft 13, the sliding contact 16 and the header 6, becomes interrupted. Thereby, the mapping electrode 30 becomes electrically disconnected from the conductor 20 during the implantation and fixation procedure, and the insulating surface layer 9 provided on the inner surface of the header 6 ensures that the mapping electrode 30 remains electrically disconnected from the conductor 20 after implantation.

Figure 3A:
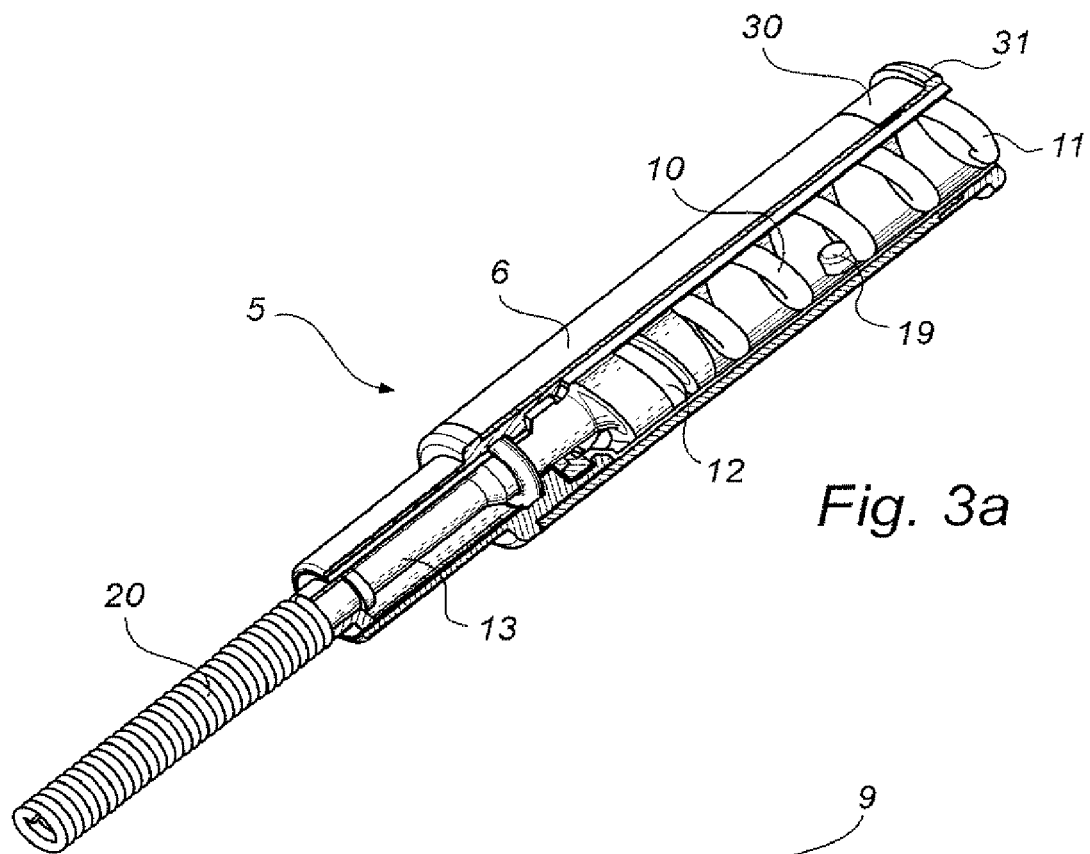
FIG. 3a is a perspective view of a distal end of an implantable lead according to a second embodiment.
Figure 3B:
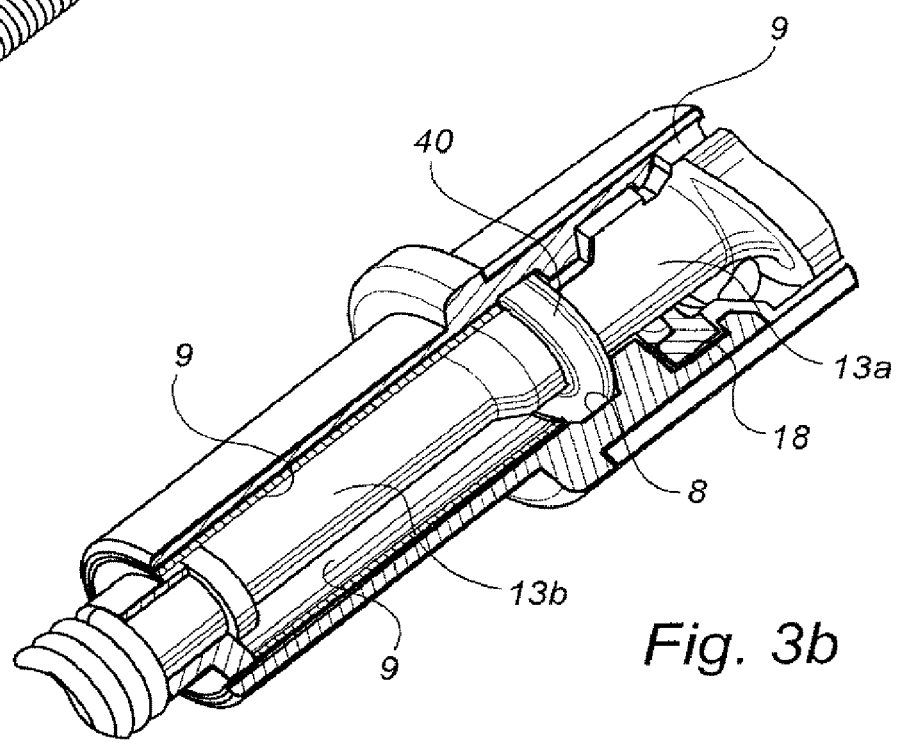

With reference to FIGS. 3a and 3b, there will now be described an implantable lead according to a second exemplifying embodiment. In this embodiment, the functions and general features of the conductor 20, helix 10, header 6, mapping electrode 30, post 19 and insulating layer 9 are generally the same as for the embodiment described above. However, in this embodiment, it is the dimensional design of the shaft 13 that provides the electrical disconnection of the mapping electrode 30 from the conductor 20.

As can be seen in the figure, the shaft 13 is in this embodiment designed with a distal end 13a having a larger diameter, and a proximal end 13b having a smaller diameter. The lead is further provided with an annular contact element 40 for providing engagement and electrical contact between the shaft 13 and a conducting surface portion 8 of the inner surface of the header 6. Thus, the contact element is electrically conducting and acts as an contact spring in biased engagement between the larger diameter portion 13a of the shaft 13 and the header 6.

The inner surface of the header 6, apart from the conducting surface portion 8 provided at the contact element 40, is provided with an electrically insulating surface layer extending from the conducting surface portion 8 to the proximal and distal end of the header 6, respectively.

When the shaft 13 during fixation of the distal end 5 of the lead is advanced in relation to the header 6, as described above, the narrower, proximal portion 13b of the shaft 13 becomes positioned at the location of the contact element 40. Since the contact element 40 has a smallest inner diameter that is larger than the outer diameter of the shaft proximal portion 13b, the contact element 40 becomes disengaged from the shaft 13 and the electrical conduction path therebetween is interrupted. Thus, the mapping electrode 30 thereby becomes electrically disconnected from the conductor 20 during the fixation of the lead.

Optionally, the proximal portion 13b of the shaft 13 may be provided with an electrically insulating surface layer to even further ensure that the contact element 40 will be electrically disengaged from the shaft 13 when the lead is implanted.

The contact element 40 could be formed from a number of different elements, as understood by the person skilled in the art. However, in the described example, the contact element 40 constitutes a toroid coil spring, such as can be purchased by Bal Seal Engineering, Inc.

Figure 4:
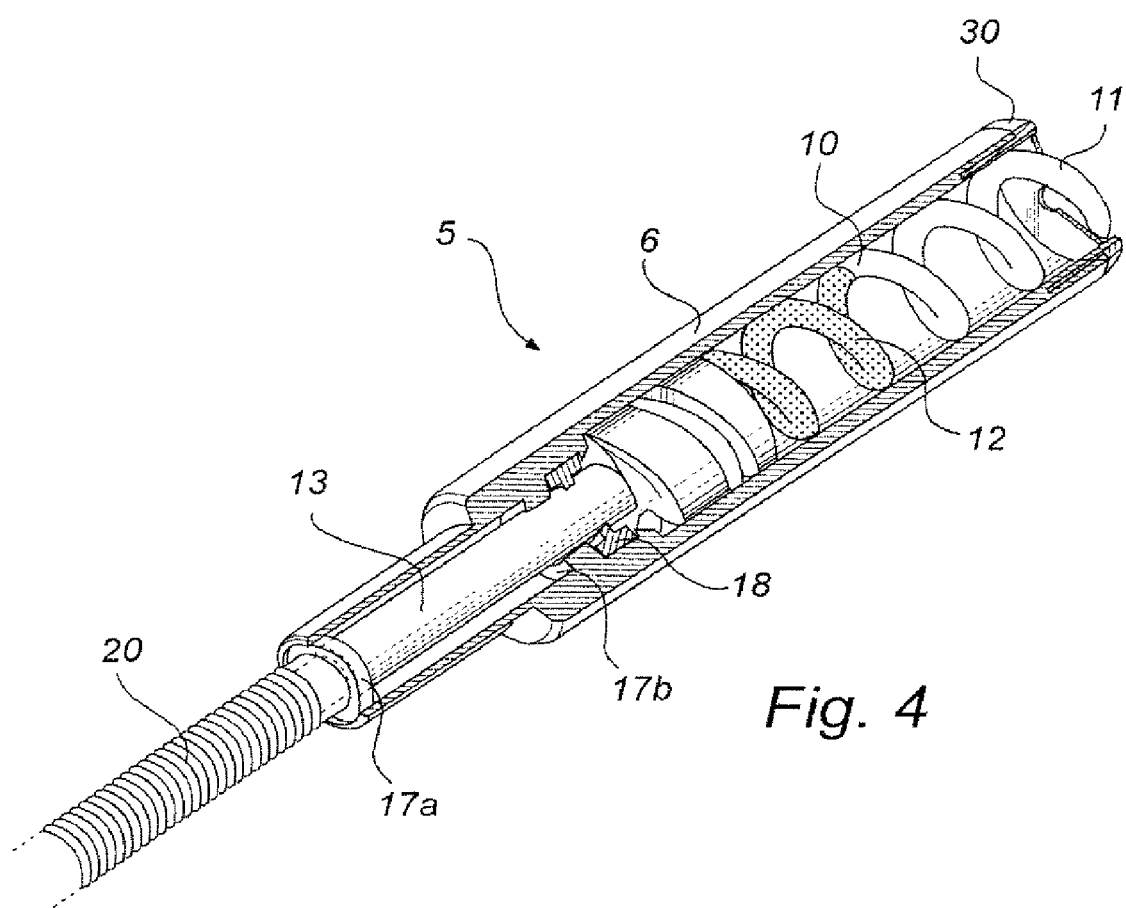
FIG. 4 is a perspective view of a distal end of an implantable lead according to a third embodiment.

Turning now to FIG. 4, there is shown an implantable lead according to a third exemplifying embodiment. In this embodiment, electrical connection between the conductor 20 and the mapping electrode 30 is provided through the direct engagement between the helix 10 and the mapping electrode 30. Thus, the helix 10 is in constant electrical connection with the conductor 20 via the shaft 13. The header 6 provides an electrical insulation between the mapping electrode 30 and the conductor 20, shaft 13, and helix 10, respectively. This can be achieved by providing relevant surface portions of the header 6, or contacting surfaces of the engaging elements, with insulating surface layers. However, it can also be achieved by forming the entire header from a dielectric or insulating material.

Furthermore, the engagement between the helix 10 and the mapping electrode 30 is provided by forming the mapping electrode 30 as a washer in which a circular sector portion of the washer has been removed for allowing the distal end of the helix 10 to be advanced through the washer, i.e. the mapping electrode 30. The engagement not only provides an electrical connection between the mapping electrode and the helix, it does also provide a counterforce during rotation of the helix 10, such that the helix 10 will be advanced through the header 6 and the mapping electrode through rotation of the helix 10.

The helix 10 has a distal portion 11 for fixation to the heart tissue and for transmitting electrical signals to and from the heart, and a proximal portion 12. The proximal portion 12 is provided with an electrically insulating surface, provided by a suitable surface coating, which is indicated by the dotted pattern in the figure. Upon rotation of the helix 10 in relation to the header 6 and mapping electrode 30, the distal end 11 of the helix will be advanced beyond the mapping electrode 30, and the proximal portion 12 will be brought into engagement with the mapping electrode 30. Thereby, the conduction path between the mapping electrode 30 and the helix 10 will be interrupted, and the mapping electrode 30 will be electrically disconnected from the conductor 20 during implantation and fixation of the distal end 5 of the lead in the heart.

Since the engagement between the mapping electrode 30 and the helix 10 provides the advancing motion of the helix 10, the stopper 19, as referred to in the examples described above, may be omitted. Furthermore, in the present example, a stopper element 17a attached to the shaft and a stopper surface 17b attached to the header are provided to limit the extent to which the helix may be extended beyond the distal end of the header.

Figure 5A:
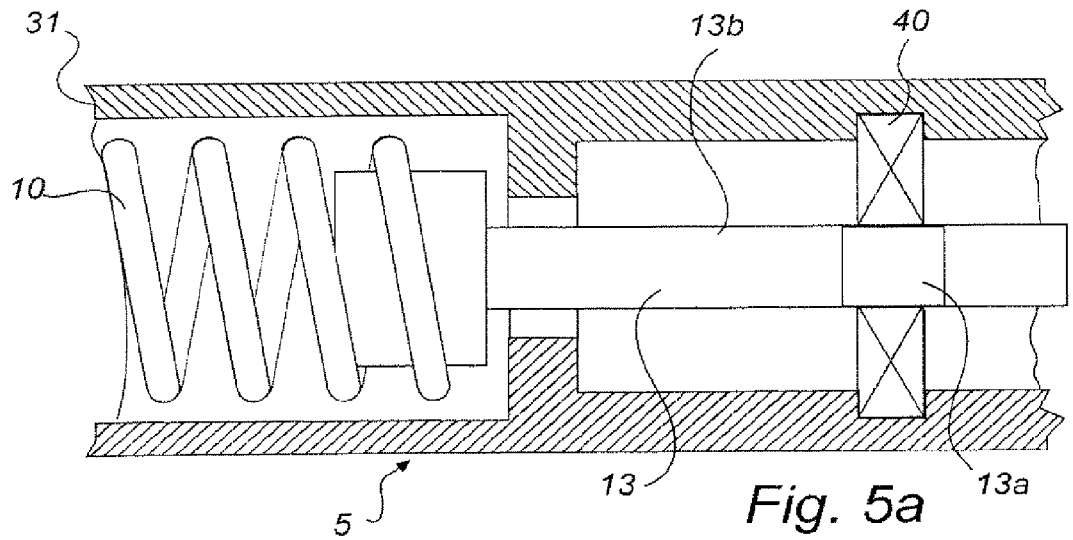
FIGS. 5a and 5b are schematical illustrations of a general principle of operation according to several embodiments.
Figure 5B:
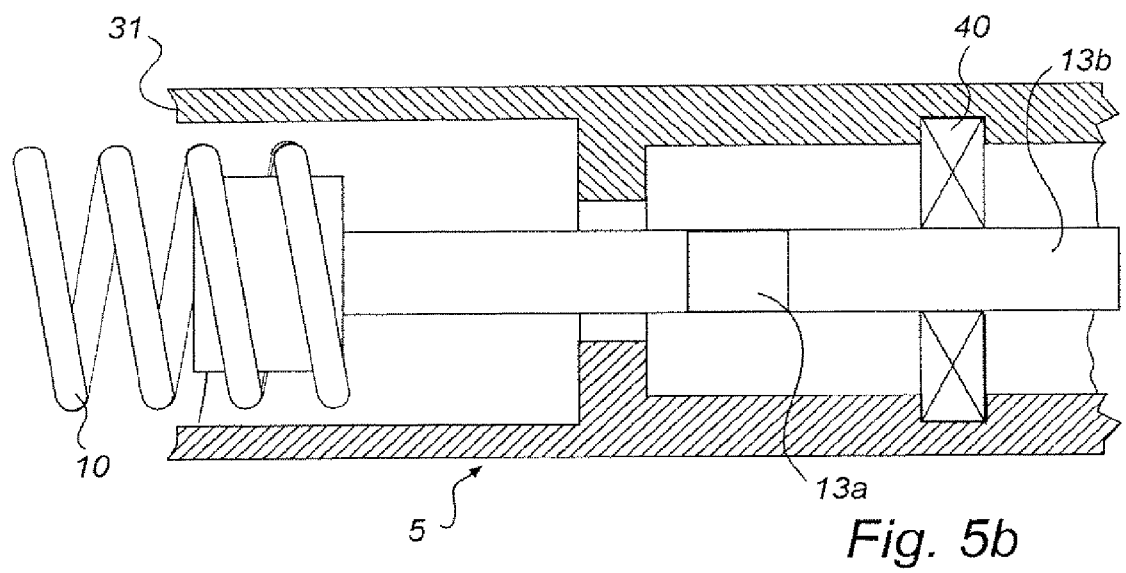

Turning finally to FIGS. 5a and 5b, there is shown schematical illustrations of a general principle of operation for embodiments of the present invention. Thus, the purpose of FIGS. 5a and 5b is not to present a detailed description of a further exemplifying embodiment, but rather to provide a simplified illustration of how the disconnection of the mapping electrode may be achieved during fixation of the implantable lead.

In FIG. 5a, the distal end 5 of an implantable lead is shown, in which a stimulating electrode, such as a helix 10, is illustrated in a retracted state before and during the initial stages of implantation. Then, the helix 10 is coupled to a shaft 13, which is provided with an electrically conducting surface portion 13a. The electrically conducting surface portion 13a is positioned such that engagement and electrically conducting contact with a contact element 40 is provided, which in turn is electrically connected to a mapping electrode surface 31. Thus, at this point, an uninterrupted conduction path is provided between the mapping electrode surface 31 and a conductor (not shown in this illustration) electrically connected to the shaft 13.

In FIG. 5b, the distal end 5 of the implantable lead is shown when the helix 10 has been brought to an extended state, such as during the later stages of or after implantation. Here, the electrically conducting surface portion 13a has been brought, by the advancing motion of the helix 10, into a position where there no longer is engagement and electrically conducting contact between the conducting surface portion 13a and the contact element 40. Thus, at this point, the conduction path between the mapping electrode surface 31 and the conductor (not shown in this illustration) has been interrupted and the mapping electrode has been electrically disconnected.

As understood by the person skilled in the art, the insulating or non-conducting portions and surface layers could be provided in a variety of different manners and from a variety of different materials. However, the present invention is not restricted to any particular manner or material. The examples given above are merely for exemplifying purposes.

Although the invention has been described with reference to specific examples thereof, many different alterations, modifications and the like will become apparent for those skilled in the art. The described examples are therefore not intended to limit the scope of the invention, as defined by the appended claims.

We claim as our invention:

1. An implantable lead for delivering electrical stimuli to a human heart, comprising a proximal end for connection to an implantable medical device, a distal end for fixation in the myocardium of a human heart, an insulating flexible tube extending from the proximal to the distal end, and a conductor arranged in said flexible tube and extending from the proximal to the distal end for conducting said electrical stimuli from the medical device to the heart and/or for conducting sensed intrinsic cardiac signals from the heart to the medical implant, said distal end comprising a fixation arrangement for said fixation of the distal end in the myocardium, a stimulating electrode for transmitting said electrical stimuli to the myocardium after implantation, and a mapping electrode for transmitting said electrical stimuli to the myocardium and/or for sensing intrinsic cardiac activity during implantation for finding a suitable fixation position in the myocardium, wherein said mapping electrode is electrically connected to said conductor during implantation, and said lead being configured to electrically disconnect the mapping electrode from the conductor.

2. The implantable lead as claimed in claim 1, wherein the lead is configured to provide said electrical disconnection, in connection with implantation when a suitable fixation position has been found and the distal end is located within the heart, through activation of the fixation arrangement during fixation of the distal end.

3. The implantable lead as claimed in claim 1, further comprising: a header at said distal end, the header comprising said mapping electrode arranged at a distal end of the header, wherein said conductor and said flexible tube are attached to the proximal end of said header, the header element further comprising a connection arrangement for electrical connection between the mapping electrode and the conductor, and wherein at least a part of the connection arrangement is arranged to be movable such that the conductor is electrically disconnected from the mapping electrode.

4. The implantable lead as claimed in claim 3, wherein the header element further comprises a tubular element electrically connected to the mapping electrode, and a shaft arrangement electrically connected to the conductor and arranged inside the tubular portion, wherein the tubular element and the shaft arrangement forming parts of said connection arrangement, wherein the shaft arrangement is configured to be rotated or advanced in relation to the tubular element from a first position, in which the shaft arrangement and the tubular element are electrically connected, to a second position in which electrical connection between the shaft arrangement and the tubular element is interrupted, thereby electrically disconnecting the conductor from the mapping electrode.

5. The implantable lead as claimed in claim 4, wherein at least one of the shaft arrangement and the tubular portion comprises an electrically insulating portion, and wherein said insulating portion in the second position is positioned in the conduction path between the conductor and the mapping electrode, thereby electrically disconnecting the conductor from the mapping electrode.

6. The implantable lead as claimed in claim 5, wherein the tubular portion comprises said insulating portion and the shaft arrangement comprises a sliding contact for the connection between the shaft arrangement and the tubular portion and, wherein the sliding contact abuts said insulating portion of the tubular portion in said second position.

7. The implantable lead as claimed in claim 4, wherein the shaft arrangement is configured to be moved from a first position, in which the shaft arrangement is in abutment, directly or via a contact element, with the tubular portion, to a second position in which the shaft arrangement is not in abutment with the tubular portion, such that electrical connection between the shaft arrangement and the tubular element is interrupted.

8. The implantable lead as claimed in claim 7, wherein the shaft arrangement comprises a shaft of a first diameter at a first location along the shaft, such that abutment between the shaft arrangement and the tubular portion is provided at said first location, and a second, smaller diameter at a second location along the shaft, such that there is no abutment between the shaft arrangement and the tubular portion at said second location.

9. The implantable lead as claimed in claim 7, wherein said shaft arrangement is in abutment with the tubular portion via a contact element.

10. The implantable lead as claimed in claim 1, wherein said stimulating electrode is permanently connected to said conductor for receiving said electrical stimuli.

11. The implantable lead as claimed in claim 10, wherein said stimulating electrode is comprised in said fixation arrangement.

12. The implantable lead as claimed in claim 11, wherein said stimulating electrode is configured to be advanced in relation to the distal end of the lead such that the stimulating electrode is brought into engagement with and fixation to the myocardium of the heart.

13. The implantable lead as claimed in claim 12, wherein said lead is configured to electrically disconnect said mapping electrode during said advancement of the stimulating electrode into engagement with the myocardium.

14. The implantable lead as claimed in claim 1, wherein said conductor is electrically connected to said stimulating electrode, and wherein the stimulating electrode is configured to be moved in relation to said mapping electrode from a first position in which the stimulating and mapping electrodes are electrically connected, to a second position in which the stimulating and mapping electrodes are electrically disconnected from each other.

15. The implantable lead as claimed in claim 14, wherein the stimulating electrode is dimensioned to establish abutment with the mapping electrode in said first position, but not in said second position.

16. The implantable lead as claimed in claim 15, wherein the surface of the stimulating electrode comprises conducting portions and insulating portions, wherein the conductive surface portions are in abutment with the mapping electrode in said first position, and wherein the insulating portions are in abutment with the mapping electrode in the second position.

17. The implantable lead as claimed in claim 1, wherein the stimulating electrode comprises an extendible and retractable helix configured for extension from said distal end when rotated in relation to said distal end, such that screw-in fixation of the lead to the myocardium of the heart may be provided, and wherein the lead is configured for providing electrical disconnection by said rotation and extension of the helix during said screw-in fixation.

18. The implantable lead as claimed in claim 1, wherein the mapping electrode is provided with an annular configuration, such that a circular end surface of the mapping electrode is formed for abutment with myocardial tissue.

19. The implantable lead as claimed in claim 18, wherein an extendible and retractable helical stimulating electrode is provided at the distal end of the lead, said stimulating electrode being arranged inside the annular mapping electrode, and wherein the stimulating electrode in the retracted state is enclosed within the distal end of the lead, and in the extended state protrudes beyond the distal end of the lead and the encircling mapping electrode for screw-in fixation of the lead in myocardial tissue.

* * * * *